(12) United States Patent
Song

(10) Patent No.: US 11,123,757 B2
(45) Date of Patent: Sep. 21, 2021

(54) ESSENTIAL OIL ATOMIZER

(71) Applicant: Puzhen Life Co., Limited, Shatin (HK)

(72) Inventor: Baojie Song, New York, NY (US)

(73) Assignee: PUZHEN LIFE CO., LIMITED

( * ) Notice: Subject to any disclaimer, the term of this patent is extended or adjusted under 35 U.S.C. 154(b) by 481 days.

(21) Appl. No.: 16/033,037

(22) Filed: Jul. 11, 2018

(65) Prior Publication Data

US 2019/0299230 A1  Oct. 3, 2019

Related U.S. Application Data

(63) Continuation-in-part of application No. PCT/CN2018/081092, filed on Mar. 29, 2018, and a continuation-in-part of application No. PCT/CN2018/081091, filed on Mar. 29, 2018.

(51) Int. Cl.
| | | |
|---|---|---|
| B05B 7/04 | (2006.01) | |
| A61L 9/14 | (2006.01) | |
| B05B 7/24 | (2006.01) | |
| B05B 7/00 | (2006.01) | |

(52) U.S. Cl.
CPC .............. *B05B 7/0483* (2013.01); *A61L 9/14* (2013.01); *B05B 7/0012* (2013.01); *B05B 7/2491* (2013.01); *A61L 2209/14* (2013.01)

(58) Field of Classification Search
CPC ..... A61L 9/14; A61L 2209/14; B05B 7/0483; B05B 7/2491; B05B 7/0012
See application file for complete search history.

(56) References Cited

U.S. PATENT DOCUMENTS

| | | |
|---|---|---|
| 3,866,414 A | 2/1975 | Sturgess |
| 4,184,615 A | 1/1980 | Wright |
| 4,550,706 A | 11/1985 | Hoffman |
| (Continued) | | |

FOREIGN PATENT DOCUMENTS

| | | |
|---|---|---|
| CN | 2751868 | 1/2006 |
| CN | 201832737 | 5/2011 |
| (Continued) | | |

*Primary Examiner* — Sean E Conley
(74) *Attorney, Agent, or Firm* — Dorsey & Whitney LLP

(57) ABSTRACT

An essential oil reflux-type atomizer comprising the following structures: chassis (10), housing (30), atomization chamber (310), gas pump (21), gas tube (22), gas nozzle (23), oil nozzle (24), filter atomization mechanism (40). The filter atomization mechanism (40) is installed in the housing (30) and has a plurality of filter housings (41). A lower end of each of the filter housings (40) has one or more through holes (411). When the gas nozzle (23) ejects an airflow, the airflow draws out the essential oil through the oil nozzle (24) to form a mixed airflow which passes through each of the filter housings (41) successively. Larger essential oil droplets in the airflow are filtered by each of the filter housings (41) to be recycled, while the atomized essential oil gas will pass through the through holes (411) of each of the filter housings to be dispensed. At the same time, the essential oil droplets in the through holes (411) are re-atomized by the airflow to improve the atomization performance. The atomization chamber (310) comprises a guide board guiding the airflow from the gas nozzle (23) upwards towards the filter atomization mechanism (40).

44 Claims, 4 Drawing Sheets

(56) References Cited

U.S. PATENT DOCUMENTS

| | | | |
|---|---|---|---|
| 4,974,573 A | 12/1990 | Jensen | |
| 7,878,418 B2 | 2/2011 | Sevy | |
| 8,857,735 B2 | 10/2014 | Rosener et al. | |
| 9,211,357 B1 | 12/2015 | Li | |
| 9,358,557 B2 | 6/2016 | Young et al. | |
| 9,415,130 B2 | 8/2016 | Sevy | |
| 9,421,295 B1 * | 8/2016 | Li | A61L 9/125 |
| 2002/0068023 A1 | 6/2002 | Davis | |
| 2003/0132311 A1 | 7/2003 | Dorendorf et al. | |
| 2005/0116059 A1 | 6/2005 | Lin | |
| 2006/0145368 A1 | 7/2006 | Thomas | |
| 2007/0163577 A1 | 7/2007 | Van Roemburg | |
| 2007/0242464 A1 | 10/2007 | Yu et al. | |
| 2008/0121660 A1 | 5/2008 | Ophardt | |
| 2011/0259974 A1 | 10/2011 | Cooper et al. | |
| 2016/0000959 A1 | 1/2016 | Sevy | |
| 2016/0361678 A1 | 12/2016 | Blackley | |
| 2017/0246336 A1 | 8/2017 | Suissa et al. | |
| 2020/0016344 A1 | 1/2020 | Scheck et al. | |
| 2020/0022411 A1 | 1/2020 | Krietzman | |
| 2020/0139387 A1 | 5/2020 | Song | |

FOREIGN PATENT DOCUMENTS

| | | | |
|---|---|---|---|
| CN | 202184967 | | 4/2012 |
| CN | 202741276 | | 2/2013 |
| CN | 103041480 | A | 4/2013 |
| CN | 103230638 | | 8/2013 |
| CN | 103375230 | | 10/2013 |
| CN | 203436642 | | 2/2014 |
| CN | 203916959 | | 11/2014 |
| CN | 204072864 | | 1/2015 |
| CN | 204072868 | | 1/2015 |
| CN | 204396240 | U | 6/2015 |
| CN | 105013059 | A | 11/2015 |
| CN | 107758798 | A | 3/2016 |
| CN | 105536021 | A | 5/2016 |
| CN | 105561367 | A | 5/2016 |
| CN | 106423613 | A | 2/2017 |
| CN | 205966339 | | 2/2017 |
| CN | 206046319 | U | 3/2017 |
| TW | 411243 | U | 9/2011 |

* cited by examiner

ESSENTIAL OIL ATOMIZER

CROSS-REFERENCE TO RELATED APPLICATIONS

This application is a continuation-in-part of International Patent Application No. PCT/CN2018/081092, filed on Mar. 29, 2018 and a continuation-in-part of International Patent Application No. PCT/CN2018/081091, filed on Mar. 29, 2018. The contents of the above-mentioned patent applications are herein incorporated by reference.

TECHNICAL FIELD

The present invention relates to the field of atomizer, and more particularly to an airflow guided essential oil reflux-type atomizer.

BACKGROUND

In daily life, essential oils are often used to improve the surrounding environment or to perform medical treatment, such as sterilization, disinfection or changing environmental odor, etc. When using the essential oils, an atomizer is often used to atomize the essential oils for facilitating diffusion of the essential oils into the environment.

SUMMARY

A conventional essential oil atomizer typically ejects a high-speed airflow to extract an essential oil from an essential oil bottle and transfer the essential oil out of the atomizer to achieve atomization. However, the inventors found that this atomization method results in larger droplets of essential oil in the atomized gas and the atomization performance is poor. In addition, the large essential oil droplets will cause a lot of waste if they are dispensed. To reduce the waste of essential oils, a filter is often used for filtering the atomized airflow mixed with the essential oil droplets so as to recycle the essential oil droplets. However, the inventors found that, since the space of the essential oil atomization chamber is generally small, the mixed airflow may directly hit and accumulate in an area of the sidewall of the atomization chamber facing the gas nozzle. With subsequent airflow hitting the same area, the essential oil droplets in the area can be blown and splashed to the filter, thereby blocking the filter, reducing the efficiency of filtration, and causing waste.

An object of the present invention is to provide an airflow guided essential oil reflux-type atomizer in order to solve the problem that the essential oil atomization performance in the prior art is poor, causing waste of essential oil. Another object of the present invention is to solve the problem that the essential oil droplets splashing in the atomization chamber of an essential oil atomizer that may block the filters and cause waste of the essential oil.

In one aspect, the present invention features an essential oil atomizer that includes: a chassis; a housing connected to the chassis and having an atomization chamber, wherein the housing includes a dispensing opening connected to the atomization chamber, and a lower end of the housing is provided with a connection opening for connecting an essential oil bottle; an oil nozzle for extracting essential oil from an essential oil bottle, wherein the oil nozzle is located on the housing, and an upper end of the oil nozzle protrudes into the atomization chamber; a gas pump (e.g., air pump) located in the chassis; a gas tube connected to the gas pump; a gas nozzle connected to the gas pump through the gas tube and having an outlet, wherein the outlet of the gas nozzle is located adjacent to the upper end of the oil nozzle and is configured to direct an airflow exiting the gas pump to the upper end of the oil nozzle; and a filter atomization mechanism in the housing for filtering essential oil droplets in the airflow from the atomization chamber to the dispensing opening, wherein the filter atomization mechanism is located in the atomization chamber; the filter atomization mechanism includes a plurality of filter housings through which the airflow passes successively, and the lower end of each of the filter housings include one or more through holes for filtering the essential oil droplets in the airflow.

In some embodiments, each of the filter housings is cylindrical.

In some embodiments, the diameters of the plurality of filter housings are reduced successively.

In some embodiments, the plurality of filter housings are concentrically arranged.

In some embodiments, the plurality of filter housings include an innermost filter housing, and the innermost filter housing is connected to the dispensing opening.

In some embodiments, the closest distance between the sidewalls of two adjacent filter housings is from 1.5 to 10 mm.

In some embodiments, the plurality of filter housings include an outermost filter housing, and the distance between the bottom of the outermost filter housing and the oil nozzle is more than 2 mm.

In some embodiments, the bottom board of each of the filter housings is curved, with the central part of the bottom boards arched upward.

In some embodiments, the through holes of two adjacent filter housings are mutually staggered.

In some embodiments, the filter atomization mechanism further includes a fixing board installed in the atomization chamber, and the fixing board includes a plurality of connection rings for connecting the upper ends of the filter housings.

In some embodiments, the fixing board includes an air outlet located inside the innermost connection ring.

In some embodiments, each of the connection rings includes a first thread.

In some embodiments, the upper end of each of the filter housings includes a second thread for connecting to the corresponding first thread.

In some embodiments, the plurality of filter housings include an innermost filter housing, and the innermost filter housing and the fixing board are integrally formed.

In some embodiments, the fixing board is integrally connected to the sidewall of the innermost layer filter housing.

In some embodiments, the oil nozzle includes an opening, and the sidewall forming the opening of the oil nozzle is conical or upwardly convex shaped.

In some embodiments, the outlet axis of the gas nozzle is directed towards the opening of the oil nozzle and at least a portion of a sidewall forming the opening of the oil nozzle.

In some embodiments, the outlet axis of the gas nozzle and the outlet axis of the oil nozzle forms an angle that is less than 90 degrees.

In some embodiments, a guide board for guiding airflow jetted by the gas nozzle upward is arranged in the atomization chamber and facing the gas nozzle, and the guide board forms an inclined plane relative to the outlet of the gas nozzle.

In some embodiments, the guide board is integrally connected with a sidewall of the atomization chamber.

In some embodiments, the lower end of the atomization chamber includes a return funnel, the lower end of the return funnel including an outlet tube protruding into the connection opening.

In some embodiments, the oil nozzle is located at a corresponding position of the outlet tube, and the guide board is connected with the upper end of the return funnel.

In some embodiments, the lower end of the oil nozzle is connected with a connection sleeve, a tube being detachably inserted into the connection sleeve.

In some embodiments, a connection tube is arranged to connect the gas tube to the gas nozzle, wherein the connection tube is configured to transfer airflow from the gas tube to the gas nozzle.

In some embodiments, a sealing ring is arranged to secure the connection between the gas nozzle and the connection tube.

In some embodiments, the housing includes a main housing installed at the chassis and an outer cover installed at the main housing, and the main housing includes the atomization chamber and one or more openings, and the outer cover covers the main housing.

In some embodiments, the outer cover includes an opening connected to the dispensing opening.

In some embodiments, the connection opening is arranged at a bottom of the main housing.

In some embodiments, the connection opening includes a threaded sleeve for connecting the essential oil bottle.

In another aspect, the present invention features an essential oil atomizer that includes: a chassis; a housing connected to the chassis and having an atomization chamber, wherein the housing includes a dispensing opening connected to the atomization chamber, and a lower end of the housing is provided with a connection opening for connecting an essential oil bottle; an oil nozzle for extracting essential oil from an essential oil bottle, wherein the oil nozzle is located on the housing, and an upper end of the oil nozzle protrudes into the atomization chamber; a gas pump located in the chassis; a gas tube connected to the gas pump; a gas nozzle connected to the gas pump through the gas tube and having an outlet, wherein the outlet of the gas nozzle is located adjacent to the upper end of the oil nozzle and is configured to direct an airflow exiting the gas pump to the upper end of the oil nozzle; and a guide board located in the atomization chamber facing the gas nozzle; wherein the guide board forms an angle with the outlet axis of the gas nozzle, the guide board is connected to the sidewall of the atomization chamber, and the guide board is configured to guide the airflow from the gas nozzle upward to the dispensing opening.

In some embodiments, the guide board is integrally connected to the sidewall of the atomization chamber.

In some embodiments, the angle between an extension line of the outlet axis of the gas nozzle and a tangent line to the surface of the guide board at the intersection of the said extension line and the guide board is 15-35 degrees.

In some embodiments, the lower end of the atomization chamber includes a return funnel, the lower end of the return funnel includes an outlet tube protruding into the connection opening.

In some embodiments, the oil nozzle is located at a corresponding position of the outlet tube, and the guide board is connected with the upper end of the return funnel.

In some embodiments, the guide board is integrally connected with the upper end of the return funnel.

In some embodiments, the guide board is flat or curved.

In some embodiments, the oil nozzle includes an opening, and the sidewall forming the opening of the oil nozzle is conical or upwardly convex shaped.

In some embodiments, the outlet axis of the gas nozzle is directed towards the opening of the oil nozzle and at least a portion of a sidewall forming the opening of the oil nozzle.

In some embodiments, the outlet axis of the gas nozzle and the outlet axis of the oil nozzle forms an angle that is less than 90 degrees.

In some embodiments, the lower end of the oil nozzle is connected with a connection sleeve, a tube being detachably inserted into the connection sleeve.

In some embodiments, a connection tube is arranged to connect the gas tube to the gas nozzle, wherein the connection tube is configured to transfer airflow from the gas tube to the gas nozzle.

In some embodiments, a sealing ring is arranged to secure the connection between the gas nozzle and the connection tube.

In some embodiments, the housing includes a main housing installed at the chassis and an outer cover installed at the main housing, and the main housing includes the atomization chamber and one or more openings, and the outer cover covers the main housing.

In some embodiments, the outer cover includes an opening connected to the dispensing opening.

In some embodiments, the connection opening is arranged at a bottom of the main housing.

In some embodiments, the connection opening includes a threaded sleeve for connecting the essential oil bottle.

Compared to conventional essential oil atomizer, the airflow guided essential oil reflux-type atomizer of the present invention has one or more of the following beneficial effects: First, by providing the filter atomization mechanism in the atomization chamber, when an airflow is pumped out of the gas pump through the gas nozzle, the airflow extracts the essential oil from the essential oil bottle through the oil nozzle, and atomize the essential oil to form a mixed airflow; when the mixed airflow passes through each of the filter housings of the filter atomization mechanism successively, larger essential oil droplets in the airflow are filtered by each of the filter housings to be recycled, thereby reducing waste of the essential oil, while smaller atomized essential oil droplets will pass through the through hole of each of the filter housings to be dispensed out the atomizer into the environment; and when the essential oil droplets in the airflow are located in each of the through holes, the pressure difference between two sides of the filter housing can create an airflow in each of the through holes to re-atomize these essential oil droplets to improve the atomization performance. Second, by providing the guide board and the filter in the atomization chamber, the mixed airflow (which includes a mixture of the airflow from the gas pump and the essential oil from the oil bottle) can hit the guide board and be guided to flow upward to the filter atomization mechanism, where the larger essential oil droplets are filtered and recycled to reduce waste; at the same time, the guide board can also collect some of the essential oil droplets from the mixed airflow, reducing oil splashing which may block the filter to ensure filtration efficiency.

BRIEF DESCRIPTION OF THE DRAWINGS

FIG. 1 is a sectional structure view of the essential oil atomizer provided by a first embodiment of the present invention.

FIG. 2 is an enlarged view of the gas nozzle and the oil nozzle of the essential oil atomizer shown in FIG. 1.

Figure 1:
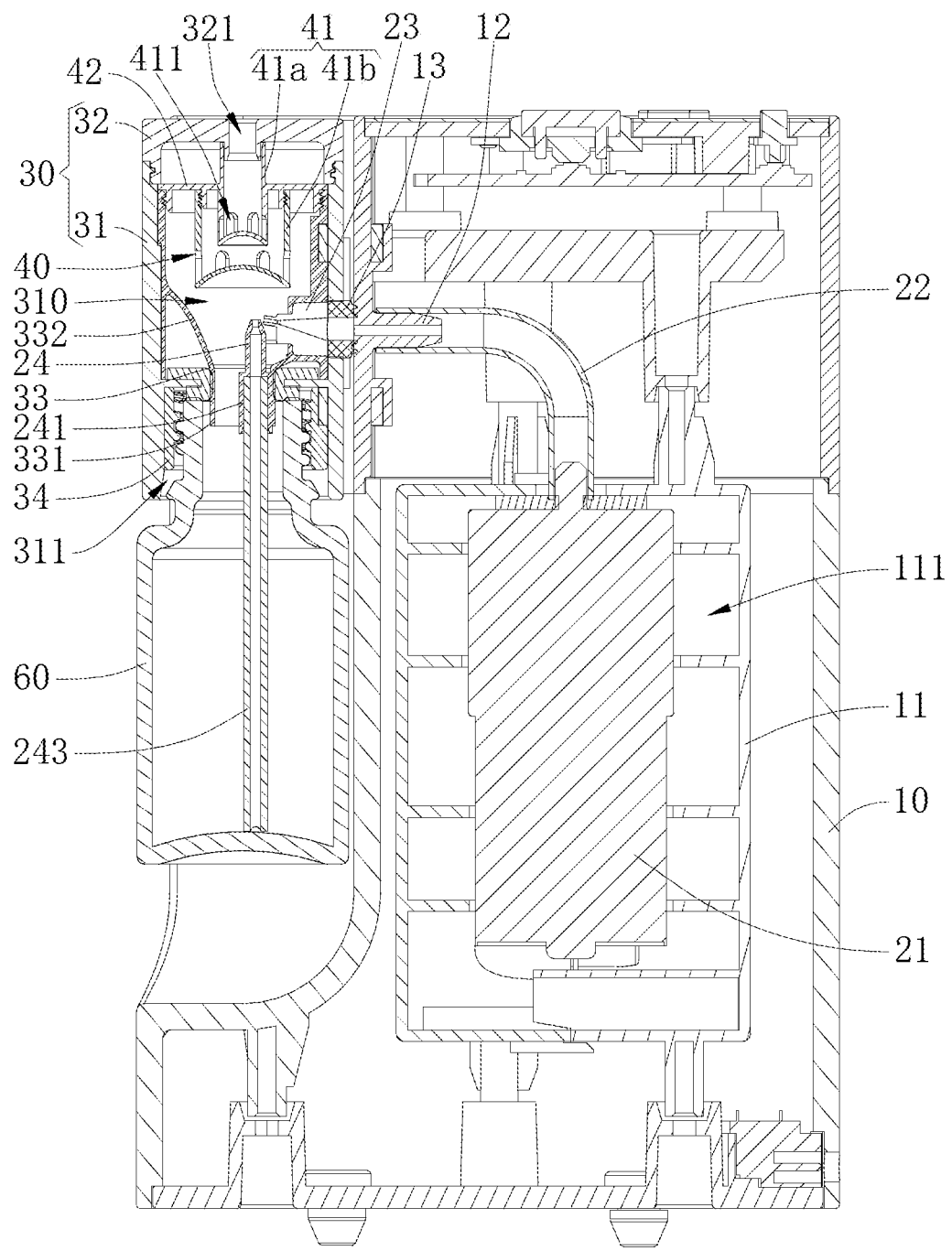

The reference numerals in FIGS. 1-5 are referred to as follows:

10—Chassis; 11—supporting frame; 111—heat dissipation channel; 12—connection tube; 13—sealing ring;

21—gas pump; 22—gas tube; 23—gas nozzle; 231—outlet; 24—oil nozzle; 241—connection sleeve; 242—side wall; 243—oil tube;

30—housing; 31—main housing; 310 atomization chamber; 311—connection opening; 32—outer cover; 321—dispensing opening; 33—return funnel; 331—outlet tube; 332—guide board; 34—thread sleeve;

40—filter atomization mechanism; 41—filter housing; 41*a*—inner layer filter housing; 41*b*—outer layer filter housing; 411—through hole; 412—bottom board; 42—fixing board; 421—connection ring; 422—fixing ring;

60—essential oil bottle.

DETAILED DESCRIPTION OF THE EMBODIMENTS

The present invention is described hereinafter with reference to the accompanying drawings and embodiments. It should be understood that the embodiments described herein are only intended to illustrate but not to limit the present invention.

It is noted that when a component is referred to as being "fixed to," "installed on," "arranged on" or "disposed on" another component, it can be directly or indirectly fixed on another component. When a component is referred to as being "connected to" another component, it can be directly or indirectly connected to the other component.

In addition, the terms "first" and "second" are for illustrative purposes only and should not be construed as indicating or implying a relative importance or indicating the quantity of technical features. Therefore, a feature that is qualified as "first" and "second" may expressly or implicitly include one or more of such a feature. In the description of the present invention, "multiple" means two or more, unless otherwise specifically defined.

Unless specified otherwise, it should be understood that, "length", "width", "upper", "lower", "front", "back", "left" and "right", "vertical", "horizontal", "top", "bottom", "inside", "outside" and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms "install," "connected," and "connect" should be interpreted broadly unless specifically defined or limited otherwise. For example, the components may be fixedly connected or they may be detachable connected, or integral connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

Embodiment One

Figure 2:
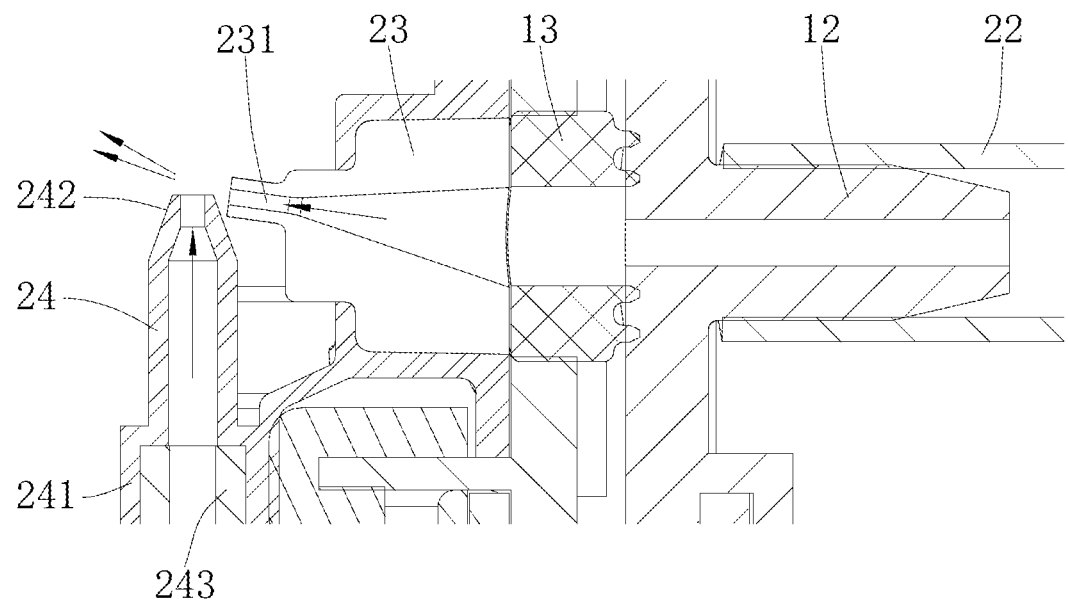
Figure 3:
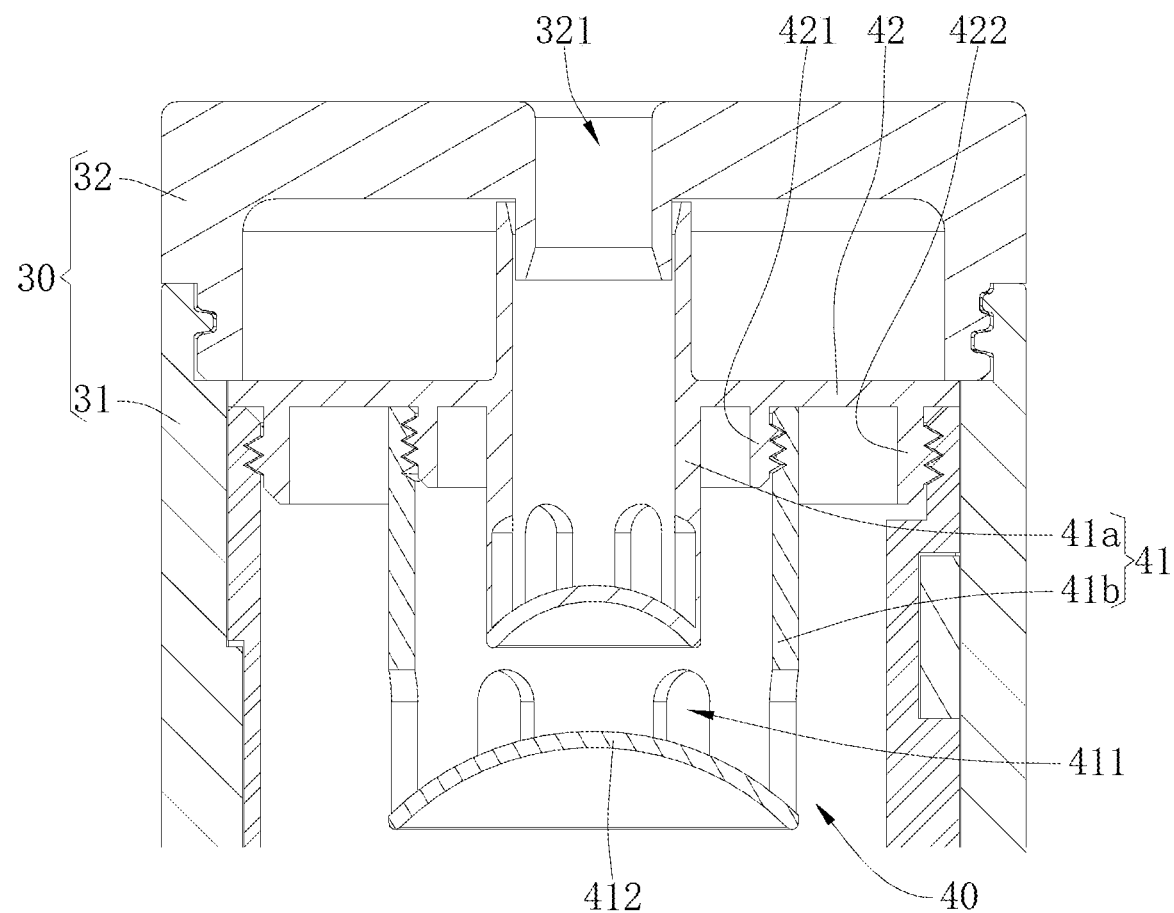
FIG. 3 is an enlarged view of the filter atomization mechanism of the essential oil atomizer shown in FIG. 1.
Figure 4:
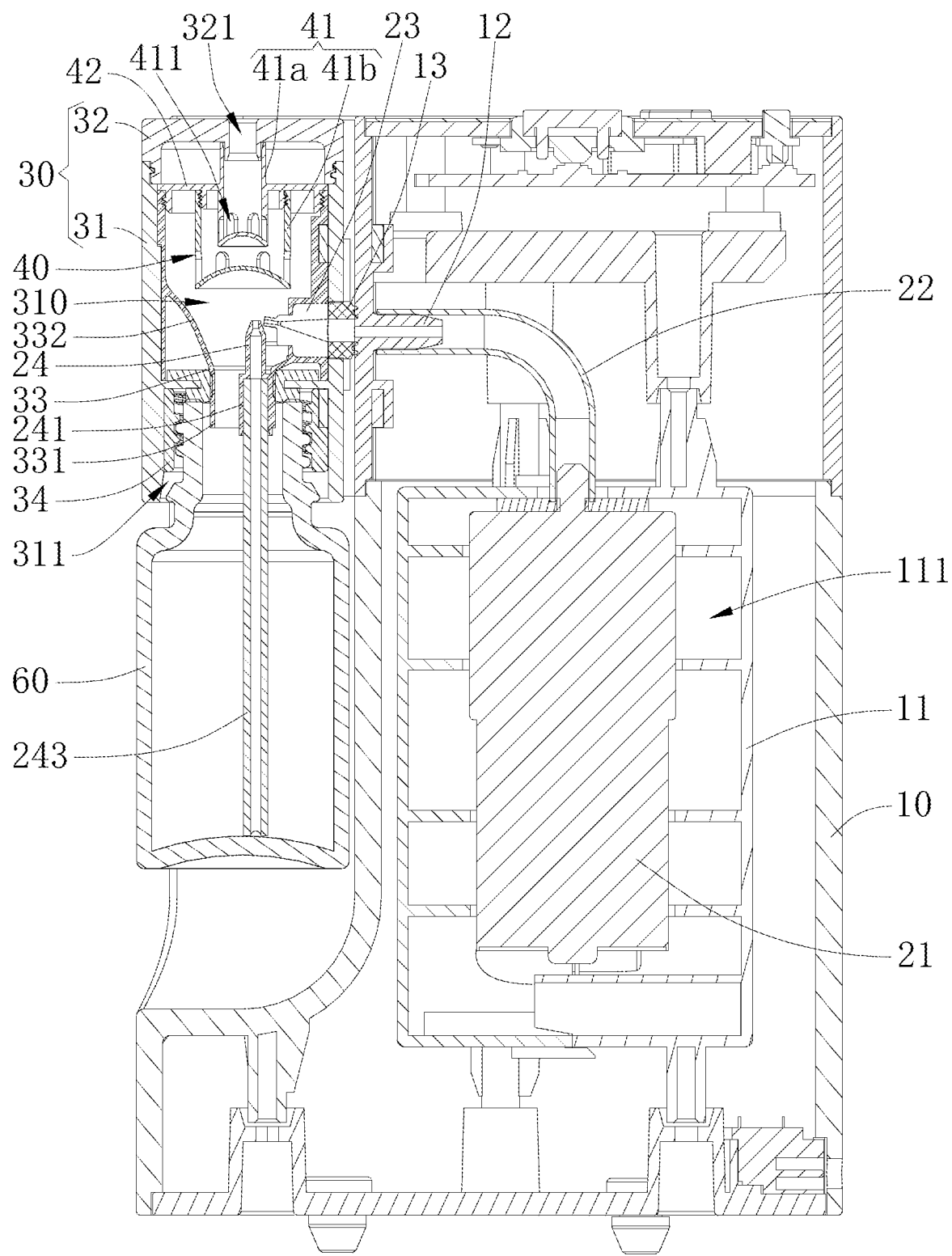
FIG. 4 is a sectional view of the essential oil atomizer provided by a second embodiment of the present invention.
Figure 5:
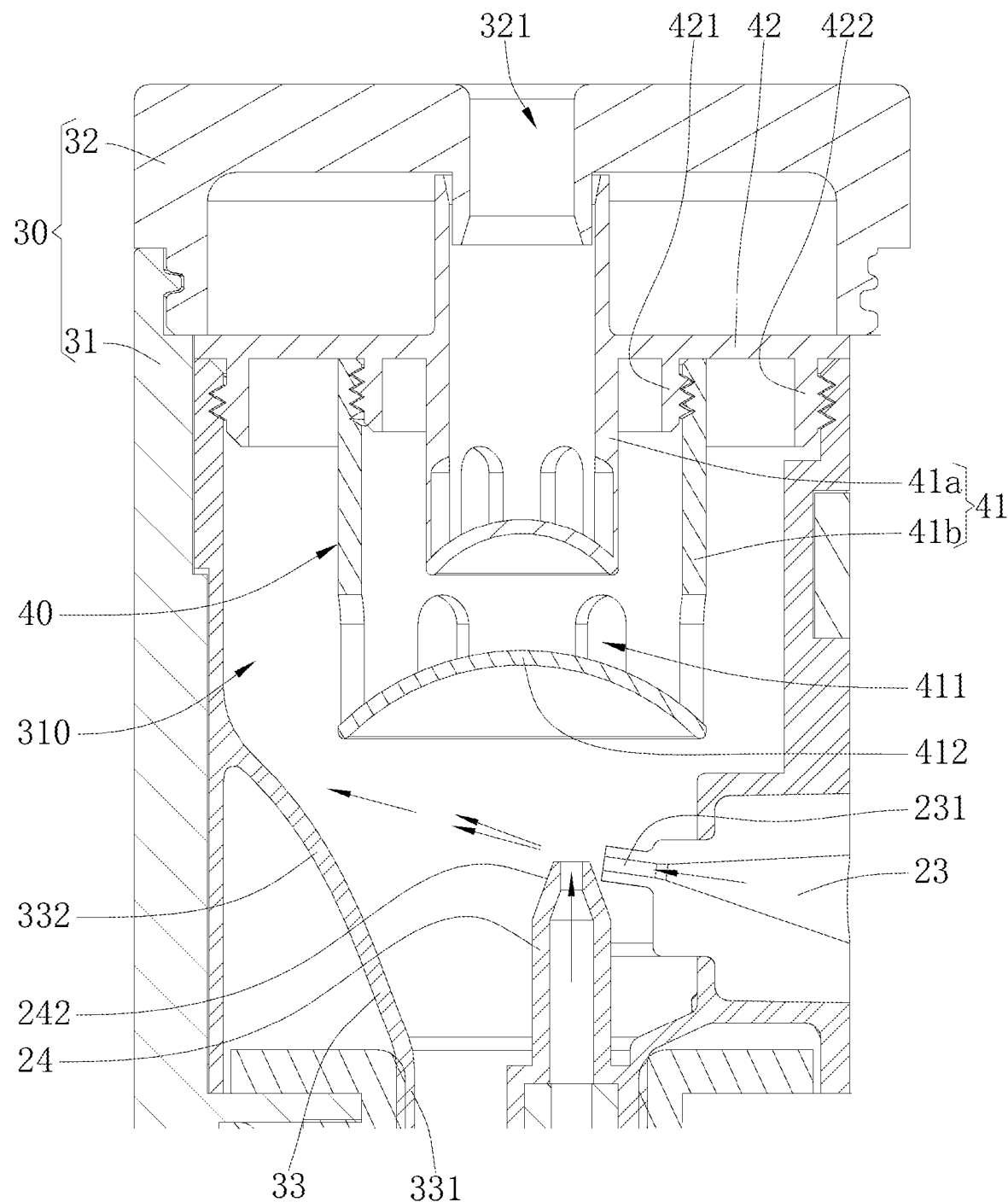
FIG. 5 is an enlarged view of the gas nozzle and the oil nozzle of the essential oil atomizer shown in FIG. 4.

FIGS. 1 to 3 represent an embodiment of an essential oil reflux-type atomizer of the present invention. The essential oil reflux-type atomizer includes a chassis 10, a housing 30, a gas pump 21, a gas tube 22, a gas nozzle 23, an oil nozzle 24, and a filter atomization mechanism 40. The housing 30 includes an atomization chamber 310 and a dispensing opening 321 connected to the atomization chamber 310. A lower end of the housing 30 includes a connection opening 311 for cooperatively connecting the essential oil bottle 60. The housing 30 is installed on the chassis 10. The gas pump 21 is also installed in the chassis 10, which supports and protects the pump 21. One end of the gas tube 22 is connected to the gas pump 21, and the other end of the gas tube 22 is connected to the gas nozzle 23. The oil nozzle 24 is located at a position corresponding to the connection opening 311 so that when the connection opening 311 is connected to the essential oil bottle 60, the essential oil can be extracted from the essential oil bottle 60 through the oil nozzle. The upper end of the oil nozzle 24 is protruded into the atomization chamber 310. An outlet 231 of the gas nozzle 23 is located adjacent to the upper end of the oil nozzle 24 and is configured to direct an airflow exiting the gas pump to the upper end of the oil nozzle. Without wishing to be bound by theory, it is believed that, when the gas pump 21 provides high pressure airflow and ejects the airflow from the gas nozzle 23, a negative pressure is formed at the upper end of the oil nozzle 24 to extract essential oil from the essential oil bottle 60 via the oil nozzle 24. The extracted essential oil droplets can then be atomized by the high-speed airflow from the gas nozzle 23 to form a mixed airflow containing essential oil droplets, which increases the pressure in the atomization chamber 310. Because the connection opening 311 and the essential oil bottle 60 are connected, the high-pressure mixed airflow in the atomization chamber 310 will be forced through the dispensing opening 321 to be dispensed into the environment.

The filter atomization mechanism 40 is arranged in the atomization chamber 310 in the housing 30 and is supported by the housing 30. The filter atomization mechanism 40 is used to filter the essential oil droplets in the airflow flowing from the atomization chamber 310 to the dispensing opening 321. When the mixed airflow in the atomization chamber 310 flows toward the dispensing opening 321, it needs to pass through the filter atomization mechanism 40, where the mixed airflow may be filtered by the filter atomization mechanism 40 to recycle larger essential oil droplets and reduce the waste of essential oils while the smaller essential oil droplets will pass through the filter atomization mechanism 40 to be dispensed through the dispensing opening 321.

In general, the filter atomization mechanism 40 includes a plurality of (e.g., two, three, or four) filter housings 41. In some embodiments, when the airflow in the atomization chamber 310 flows toward the dispensing opening 321, it passes through the filter housings 41 successively. The lower ends (e.g., at the bottom of the cylinders) of the filter housings 41 include one or more (e.g., two, three, or four) through holes 411 for filtering the essential oil droplets in the airflow. When the airflow containing essential oil droplets passes through each of the filter housings 41 successively, the larger essential oil droplets in the mixed airflow are filtered by each of the filter housings 41 and can flow back to the oil bottle through the return funnel due to gravity. The smaller essential oil droplets can pass through the through hole 411 of each of the filter housings 41 to be dispensed through the dispensing opening 321. As discussed above, the airflow from the gas nozzle 23 increases the pressure in the atomization chamber outside the filter housings 41. Without wishing to be bound by theory, it is believed that the pressure difference at two sides of the filter housing 41 creates an airflow in each of the through holes 411, such that the essential oil droplets in the through holes 411 are re-atomized by the airflow to improve the atomization efficiency. As a result, using the plurality of filter housings 41 can better filter larger essential oil droplets, further reduce waste, and improve the efficiency of filtration. In addition, it is believed that, compared to a conventional system without a filter housing, using the filter housing 41 can better return the essential oil liquid accumulated therein, and avoid oil attachment to the filter 40, and thus better recycle the filtered essential oil droplets and further reduce the waste of essential oils.

Compared to a conventional atomizer, the essential oil reflux-type atomizer of the present invention has one or more of the following beneficial effects: when the gas nozzle 23 blows out the airflow, essential oil is extracted from essential oil bottle through the oil nozzle 24, and mixed and atomized by the airflow to form a mixed airflow. When the mixed airflow passes through each of the filter housings 41 of the filter atomization mechanism 40 successively, the larger essential oil droplets in the airflow can be filtered by each of the filter housings 41 and recycled, thereby reducing waste of the essential oil. The smaller essential oil droplets can pass through each of the filter housings 41 and dispensed into the environment. The pressure difference between the two sides of the filter housing 41 creates an airflow in each of the through holes 411, therefore the essential oil droplets in the through hole 411 are re-atomized by the airflow to improve the atomization efficiency.

Further, FIGS. 1 and 3 show embodiments in which each of the filter housings 41 is cylindrical, the diameters of a plurality of the filter housings 41 are reduced successively, a plurality of the filter housings 41 are concentrically arranged, and the two adjacent filter housings 41 include an inner layer filter housing 41a is inserted into an outer layer filter housing 41b. The inner layer filter housing 41a is connected with the dispensing opening 321. The filter housings 41 are generally simple to manufacture, and easy to install. The filter housings 41 are located in the atomization chamber 310, facilitating the mixed airflow in the atomization chamber 310 to enter the filter housings 41 to be filtered and atomized. In addition, the filter housings 41 are arranged in a cylindrical shape, and one or more through holes 411 are arranged at the lower end of the filter housings 41. The inner layer filter housing 41a is inserted into the outer layer filter housing 41b. Without wishing to be bound by theory, it is believed that, when the mixed airflow enters the outer layer filter housing 41b from the through holes 411, it rotates and/or turbulently flows along the outer wall of the inner layer filter housing 41a. Thus, the atomized essential oil can rapidly diffuse, and the larger essential oil droplets will hit the outer surface of the inner layer filter housing 41a due to inertia to be blocked and filtered to improve the filtering effect. In addition, when the gas pump is not in use, the essential oil collected in the filter housings 41 forms larger droplets and returns to essential oil bottle 60 through the through holes of the filter housings 41 due to gravity and can be re-used. In some embodiments, a plurality of boards with holes (e.g., in addition to or in lieu of filter housings 41) may be used to filter the essential oil droplets in the atomization chamber. In other embodiments, the filter housings 41 may also be cup-shaped with the central part of the bottom arched downward.

In this embodiment, the number of the filter housings 41 is two, and the inner layer filter housing 41a is inserted into the outer layer filter housing 41b. In other embodiments, the number of the filter housings 41 can be three, four, or more.

Further, as shown in FIG. 3, the filter atomization mechanism 40 further includes a fixing board 42, which includes a plurality of connection rings 421 for connecting the upper ends of the filter housings 41 to the housing 30. With the connection rings 421, each of the filter housings 41 can be conveniently connected to the fixing board 42, either integrally or through threaded engagement. The fixing board 42 can be installed in the atomization chamber 310 so that the filter housings 41 can be installed in the atomization chamber 310. In some embodiments, the fixing board 42 includes a passing hole. The passing hole can be located in the innermost connection ring 421 so that when the innermost layer filter housing 41 is installed on the fixing board 42, the passing hole can receive the innermost layer filter housing 41, and thus the innermost layer filter housing 41 is connected with the dispensing opening 321.

Further, as shown in FIG. 3, the fixing board 42 can further include a fixing ring 422 around the connection rings 421. The fixing ring 422 can be connected with an inner wall of the atomization chamber 310. It is convenient to install and secure the fixing board 42 in the atomization chamber 310 through the fixing ring 422.

Furthermore, the fixing ring 422 may have installation threads. The inner wall of the atomization chamber 310 can have corresponding threads for threaded connection with the fixing ring 422.

Further, in some embodiments, one or more of the connection rings 421 may include a first thread, and the upper ends of the corresponding filter housings 41 may include a second thread corresponding to the first thread. The structure can be conveniently manufactured by methods known in the art. One or more of the filter housings 41 can be conveniently connected with the corresponding connection rings 421 through threaded engagement.

Further, as shown in FIGS. 1 and 2, the innermost layer filter housing 41 and the fixing board 42 are integrally formed. Forming the fixing board 42 integrally with the innermost layer filter housing 41 can ensure the connection strength between the innermost layer filter housing 41 and the fixing board 42. In this structure, the innermost connection ring 421 can be used as a sidewall of the inner layer filter housing 41 to reduce the space occupied. In other embodiments, the fixing board 42 and the innermost layer filter housing 41 can be two separate parts and can be connected through threaded engagement described above.

Further, as shown in FIGS. 1 and 2, a bottom board 412 of each of the filter housings 41 is curved, with the central part of the bottom board 412 arched upward. The through holes 411 are located at the lower end (e.g., defined by the sidewall and the bottom board) of the sidewall of the filter housings 41. The bottom board 412 of each of filter housings 41 is arched to allow the essential oil liquid collected in the filter housing 41 to flow toward the through holes 411 and be discharged back into the essential oil bottle 60.

Further, the through holes 411 of each of the filter housings 41 are located at the lower end of the sidewall (e.g., at the lower one-third of the sidewall) of each filter housing 41, making it convenient for manufacturing and also convenient for filtration and recycling of the essential oil droplets. Furthermore, when the bottom board 412 of a filter housing 41 has an upwardly arched arc surface, the arc surface can also guide the airflow flowing from each of the through holes 411 into the filter housing 41.

Further, the through holes 411 of two adjacent filter housings 41 can be mutually staggered. In such embodiments, when the airflow passes through the through hole 411 of the outer layer filter housing 41*b*, the larger essential oil droplets are blown onto the outer sidewall of the inner layer filter housing 41*a* to be blocked and collected to achieve better filtration. Smaller droplets have less mass and thus less inertia so that they can change directions more easily and stay with the airflow. In some embodiments, the through holes 411 in two adjacent filter housings 41 can have successively reduced diameters to filter larger essential oil droplets. For example, the diameters of the through holes 411 in the inner layer filter housing 41*a* can be smaller than those of the through holes 411 in the outer layer filter housing 41*b*. In some embodiments, the diameter of the though holes 411 of the innermost filter housing 41 ranges can be 1.6 mm-2.0 mm (e.g., 1.8 mm) while the diameter of the though holes 411 of the immediate outer filter housing 41 is can be 2.0 mm-2.4 mm (e.g., 2.2 mm). In such embodiments, the through holes 411 in the inner layer filter housing 41*a* and outer layer filter housing 41*b* can be either centrally aligned or staggered (i.e., not centrally aligned).

Further, in two adjacent filter housings 41, the bottom board of the inner layer filter housing 41*a* can be spaced from the bottom board 412 of the outer layer filter housing 41*b* so that the airflow in the gap between the inner layer filter housing 41*a* and the outer layer filter housing 41*b* can be increased, enhancing the filtration and recycling of the essential oil droplets.

Further, in two adjacent filter housings 41, the closest distance between the sidewall of the inner layer filter housing 41*a* and the sidewall of the outer layer filter housing 41*b* can range from at least 1.5 mm (e.g., at least 2 mm or at least 3 mm) to at most 10 mm (e.g., at most 9 mm or at most 8 mm). Without wishing to be bound by theory, it is believed that controlling the above distance to 1.5-10 mm can be important to minimize excessive noise when the essential oil atomizer is being used. In a preferred embodiment, the closest distance between the sidewalls of two adjacent filter housings 41 is 2.2 mm.

Further, as shown in FIGS. 1 and 2, the axial direction of the outlet 231 of the gas nozzle 23 is directed toward the top of the upper end of the sidewall 242 of the oil nozzle 24. The outlet axis of the gas nozzle and the outlet axis of the oil nozzle form an angle that is less than 90 degrees. When the airflow is ejected from the outlet 231 of the gas nozzle 23, the airflow can cover the upper end of the oil nozzle 24 to better form a negative pressure (e.g., due to Bernoulli effect) at the upper end of the oil nozzle 24, which can extract essential oil from the essential oil bottle 60. At the same time, the top of the sidewall 242 of the oil nozzle 24 can change the direction of the airflow ejected from the gas nozzle 23 (e.g., by blocking at least some of the airflow), thereby improving the atomization of the essential oil droplets drawn from the oil nozzle 24.

Further, the airflow ejected from the outlet 231 of the gas nozzle 23 is directed toward the top of the upper end of the sidewall 242 of the oil nozzle 24 from a lower position (e.g., the outlet 231 can be at a lower position than the oil nozzle 24). This arrangement can prevent the airflow ejected by the gas nozzle 23 from being blown into the oil nozzle 24, thereby facilitating extraction of the essential oil from the essential oil bottle and blowing the essential oil upward for better atomization. Further, in this embodiment, the sidewall 242 of the upper end of the oil nozzle 24 is conically shaped, guiding upward the airflow from the gas nozzle 23 so that the airflow can better atomize the essential oil drawn from the oil nozzle 24. In other embodiments, the sidewall 242 of the upper end of the oil nozzle 24 may also be a dome in shape.

Further, as shown FIG. 1, a lower end of the atomization chamber 310 includes a return funnel 33 with an outlet tube 331 at the bottom. The outlet tube 331 protrudes into the connection opening 311. The oil nozzle 24 is integrally connected to the outlet tube 331. When the connection opening 311 is connected with the essential oil bottle 60, the outlet tube 331 of the return funnel 33 is protruded into the essential oil bottle 60, so that the recycled essential oil droplets in the atomization chamber 310 can better return to the essential oil bottle 60.

Further, in this embodiment, the lower end of the return funnel 33 is connected with the inner wall of the atomization chamber 310, such that the essential oil liquid accumulated on the inner wall of the atomization chamber 310 can be easily returned to the essential oil bottle 60.

Further, as shown in FIG. 1, a lower end of the oil nozzle 24 is connected with a connection sleeve 241. An oil tube 243 can be detachably inserted in the connection sleeve 241 and can be in fluid communication with oil nozzle 24 such that essential oil can be extracted from essential oil bottle 60 to the atomization chamber 310 through the oil tube 243 and oil nozzle 24. In some embodiments, oil tubes 243 of different lengths can be used to fit different essential oil bottles 60, enhancing the adaptability of the design.

Further, as shown in FIG. 1 represent a connection tube 12 is arranged at the corresponding position of the chassis 10 to allow the gas tube 22 to be connected with the gas nozzle 23, thereby allowing airflow to travel from the gas pump 21 through the gas tube 22 and connection tube 12, and to be ejected from gas nozzle 23. The connection tube 12 is arranged in the chassis 10 such that the gas tube 22 can be securely attached to it to deliver airflow from the gas pump 21 into the atomization chamber 311.

Furthermore, in this embodiment, a sealing ring 13 is arranged between the gas nozzle 23 and the connection tube 12 to improve the sealing and minimize leaks of the connection so that substantially all the airflow in the gas tube 22 can flow through the gas nozzle 23. It is believed that this structure simplifies the manufacture and connection of the housing 30 and the chassis 10. In other embodiments, the gas nozzle 23 can also be directly connected to the gas tube 22 without using a connection tube 12. In some other embodiments, the gas nozzle 23 and the connection tube 12 can be integrally formed as a part of the chassis 10 (e.g., without using a sealing ring 13).

Further, as shown in FIGS. 1 and 3, the housing 30 includes a main housing 31 installed on the chassis 10 and an outer cover 32 installed on the main housing 31. The atomization chamber 310 is formed in the main housing 31, the outer cover 32 covers the atomization chamber 310. The outer cover 32 includes the dispensing opening 321 at the top of the housing 30. The connection opening 311 is arranged at a bottom of the main housing 31. This structure simplifies the manufacture of the housing 30 and the assembly of the parts. For example, it simplifies the installation of the oil nozzle 24, gas nozzle 23 and the filter atomization mechanism 40 onto the housing 30.

Further, as shown in FIGS. 1 and 3, the connection opening 311 is provided with a thread sleeve 34 for connecting the essential oil bottle 60. The thread sleeve 34 is arranged in the connection opening 311 to ensure easy installation and replacement of the essential oil bottle 60.

Further, as shown in FIG. 1, the chassis 10 includes a supporting frame 11. The gas pump 21 is installed on the supporting frame 11 for better fixation. The supporting frame 11 includes a plurality of heat dissipation channels 111 to improve the heat dissipation efficiency.

In some embodiments, the gas pump 21 can be a diaphragm pump. Of course, in other embodiments, the gas pump 21 can be other types of pumps, such as centrifugal pump, piston pump, and the like.

Embodiment Two

Referring to FIGS. 1 and 3, the essential oil reflux-type atomizer provided by embodiment two can have one or more of the following differences from embodiment one:

In some embodiments, a side of the atomization chamber 310 facing the gas nozzle 23 is provided with an optional guide board 332. The guide board 332 forms an inclined plane relative to the axial direction of an outlet 231 of the gas nozzle 23 and integrally connected with or formed on a sidewall of the atomization chamber 310. The guide board 332 is configured to guide the airflow jetted by the gas nozzle 23 upward. When the gas nozzle 23 ejects the air flow and extracts the essential oil to form the mixed airflow, the mixed airflow can flow towards the guide board 332 which can better guide the mixed airflow to the filter atomization mechanism 40, thereby facilitating filtration in filter atomization mechanism 40. In addition, the guide board 332 can also collect part of the essential oil droplets from the mixed airflow, reducing oil splashing (which may block the filter 40) and ensuring filtration efficiency.

Further, the guide board 332 can be connected to an upper end of the return funnel 33. This structure can make it easier for the oil droplets accumulated on the guide board 332 to return to the essential oil bottle 60 through the return funnel 33, thereby improving the efficiency of the recycling process. Further, the guide board 332 may be integrally formed with the return funnel 33 to simplify manufacture, installation and fixation.

Further, in some embodiments, the guide board 332 is flat. In some embodiments, the guide board 332 is curved.

Further, the angle between an extension line of an outlet 231 axis of the gas nozzle 23 and the tangent line at the intersection of this extension line and the guide board 332 can range from at least 15 degrees (e.g., at least 20 degrees or at least 25 degrees) to at most 35 degrees (e.g., at most 30 degrees or at most 25 degrees). For example, the angle can be about 32 degrees. In this arrangement, the guide board 332 can better guide the airflow to the guide board 332, and reduce the impact of the airflow to the guide board 332.

Further, in one specific embodiment, the closest distance between the outermost filter housing 41 and the oil nozzle 24 is at least 2 mm (e.g., at least 3 mm or at least 4 mm). This distance can reduce the oil splashing on the filter housings 41 and avoid congestion at the filter atomization mechanism 40.

The other structures of the essential oil reflux-type atomizer in the present embodiment can be the same as the corresponding structures of the essential oil reflux-type atomizer in embodiment one, and the details will not be repeated here.

The aforementioned embodiments are only preferred embodiments of the present invention, and are not intended to limit the present invention. Any modification, equivalent replacement, improvement, and so on, which are made within the spirit and the principle of the present invention, should be included in the scope of the present invention.

What is claimed is:

1. An essential oil atomizer, comprising:

a chassis;

a housing connected to the chassis and having an atomization chamber, wherein the housing comprises a dispensing opening connected to the atomization chamber, and a lower end of the housing is provided with a connection opening for connecting an essential oil bottle;

an oil nozzle for extracting essential oil from an essential oil bottle, wherein the oil nozzle is located on the housing, and an upper end of the oil nozzle protrudes into the atomization chamber;

a pump located in the chassis;

a gas tube connected to the pump;

a gas nozzle connected to the pump through the gas tube and having an outlet, wherein the outlet of the gas nozzle is located adjacent to the upper end of the oil nozzle and is configured to direct an airflow exiting the pump to the upper end of the oil nozzle; and a filter atomization mechanism in the housing for filtering essential oil droplets in the airflow from the atomization chamber to the dispensing opening, wherein the filter atomization mechanism is located in the atomization chamber; the filter atomization mechanism comprises a plurality of filter housings through which the airflow passes successively, and the lower end of each of the filter housings comprises one or more through holes for filtering the essential oil droplets in the airflow;

wherein the plurality of filter housings are concentrically arranged.

2. The essential oil atomizer of claim 1, wherein each of the filter housings is cylindrical.

3. The essential oil atomizer of claim 2, wherein the diameters of the plurality of filter housings are reduced successively.

4. The essential oil atomizer of claim 1, wherein the plurality of filter housings comprise an innermost filter housing, and the innermost filter housing is connected to the dispensing opening.

5. The essential oil atomizer of claim 4, wherein the closest distance between sidewalls of two adjacent filter housings is from 1.5 to 10 mm.

6. The essential oil atomizer of claim 5, wherein the plurality of filter housings comprise an outermost filter housing, and the closest distance between the bottom of the outermost filter housing and the oil nozzle is more than 3 mm.

7. The essential oil atomizer of claim 1, wherein a bottom board of each of the filter housings is curved and a central part of the bottom boards is arched upward.

8. The essential oil atomizer of claim 1, wherein the one or more through holes of two adjacent filter housings are mutually staggered.

9. The essential oil atomizer of claim 1, wherein the filter atomization mechanism further comprises a fixing board installed in the atomization chamber, and the fixing board comprises a plurality of connection rings for connecting upper ends of the filter housings.

10. The essential oil atomizer of claim 9, wherein the fixing board comprises an air outlet located inside an innermost connection ring of the plurality of connection rings.

11. The essential oil atomizer of claim 9, wherein one or more of the connection rings comprises a first thread.

12. The essential oil atomizer of claim 11, wherein the upper end of one or more of the filter housings comprises a second thread for connecting to the first thread.

13. The essential oil atomizer of claim 1, wherein the plurality of filter housings comprise an innermost filter housing having a fixing board, wherein at least one of the plurality of filter housings is connected to the fixing board separate from the innermost filter housing.

14. The essential oil atomizer of claim 13, wherein the fixing board is integrally connected to a sidewall of the innermost layer filter housing.

15. The essential oil atomizer of claim 1, wherein the oil nozzle comprises an opening, and a sidewall forming the opening of the oil nozzle is conical or upwardly convex shaped.

16. The essential oil atomizer of claim 1, wherein the outlet axis of the gas nozzle is directed towards the opening of the oil nozzle and at least a portion of a sidewall forming the opening of the oil nozzle.

17. The essential oil atomizer of claim 16, the outlet axis of the gas nozzle and the outlet axis of the oil nozzle forms an angle that is less than 90 degrees.

18. The essential oil atomizer of claim 1, further comprising a guide board for guiding airflow jetted by the gas nozzle upward, wherein the guide board is in the atomization chamber and facing the gas nozzle, and the guide board forms an inclined plane relative to the outlet of the gas nozzle.

19. The essential oil atomizer of claim 18, wherein the guide board is integrally connected with a sidewall of the atomization chamber.

20. The essential oil atomizer of claim 18, wherein the lower end of the atomization chamber comprises a return funnel, the lower end of the return funnel comprising an outlet tube protruding into the connection opening.

21. The essential oil atomizer of claim 20, wherein the oil nozzle is located on the sidewall of the outlet tube, and the guide board is connected with the upper end of the return funnel.

22. The essential oil atomizer of claim 1, wherein the lower end of the oil nozzle is connected with a connection sleeve, an oil tube being detachably inserted into the connection sleeve.

23. The essential oil atomizer of claim 1, further comprising a connection tube connecting the gas tube to the gas nozzle, wherein the connection tube is configured to transfer airflow from the gas tube to the gas nozzle.

24. The essential oil atomizer of claim 23, further comprising a sealing ring to secure the connection between the gas nozzle and the connection tube.

25. The essential oil atomizer of claim 1, wherein the housing comprises a main housing installed at the chassis and an outer cover installed at the main housing, and the main housing comprises the atomization chamber and one or more openings, and the outer cover covers the main housing.

26. The essential oil atomizer of claim 25, wherein the outer cover comprises an opening connected to the dispensing opening.

27. The essential oil atomizer of claim 1, wherein the connection opening is arranged at a bottom of the main housing.

28. The essential oil atomizer of claim 1, wherein the connection opening comprises a threaded sleeve for connecting the essential oil bottle.

29. An essential oil atomizer, comprising:
a chassis;
a housing connected to the chassis and having an atomization chamber, wherein the housing comprises a dispensing opening connected to the atomization chamber, and a lower end of the housing is provided with a connection opening for connecting an essential oil bottle;
an oil nozzle for extracting essential oil from an essential oil bottle, wherein the oil nozzle is located on the housing, and an upper end of the oil nozzle protrudes into the atomization chamber;
a pump located in the chassis;
a gas tube connected to the pump;
a gas nozzle connected to the pump through the gas tube and having an outlet, wherein the outlet of the gas nozzle is located adjacent to the upper end of the oil nozzle and is configured to direct an airflow exiting the pump to the upper end of the oil nozzle;
a guide board located in the atomization chamber facing the gas nozzle; wherein the guide board forms an angle with the outlet axis of the gas nozzle, the guide board is connected to the sidewall of the atomization chamber, and the guide board is configured to guide the airflow from the gas nozzle upward to the dispensing opening;
a connection tube connecting the gas tube to the gas nozzle, wherein the connection tube is configured to transfer airflow from the gas tube to the gas nozzle; and
a sealing ring to secure the connection between the gas nozzle and the connection tube.

30. The essential oil atomizer of claim 29, wherein the guide board is integrally connected to the sidewall of the atomization chamber.

31. The essential oil atomizer of claim 29, wherein the angle between an extension line of the outlet axis of the gas nozzle and a tangent line to the surface of the guide board at the intersection of the said extension line and the guide board is 15-35 degrees.

32. The essential oil atomizer of claim 29, wherein the lower end of the atomization chamber comprises a return funnel, the lower end of the return funnel comprises an outlet tube protruding into the connection opening.

33. The essential oil atomizer of claim 32, wherein the oil nozzle is integrally connected to the outlet tube, and the guide board is connected with the upper end of the return funnel.

34. The essential oil atomizer of claim 33, wherein the guide board is integrally connected with the upper end of the return funnel.

35. The essential oil atomizer of claim 29, wherein the guide board is flat or curved.

36. The essential oil atomizer of claim 29, wherein the oil nozzle comprises an opening, and the sidewall forming the opening of the oil nozzle is conical or upwardly convex shaped.

37. The essential oil atomizer of claim 29, wherein the outlet axis of the gas nozzle is directed towards the opening of the oil nozzle and at least a portion of a sidewall forming the opening of the oil nozzle.

38. The essential oil atomizer of claim 37, the outlet axis of the gas nozzle and the outlet axis of the oil nozzle forms an angle that is less than 90 degrees.

39. The essential oil atomizer of claim 29, wherein the lower end of the oil nozzle is connected with a connection sleeve, an oil tube being detachably inserted into the connection sleeve.

40. The essential oil atomizer of claim 29, further comprising a connection tube connecting the gas tube to the gas nozzle, wherein the connection tube is configured to transfer airflow from the gas tube to the gas nozzle.

41. The essential oil atomizer of claim 29, wherein the housing comprises a main housing installed at the chassis and an outer cover installed at the main housing, and the main housing comprises the atomization chamber and one or more openings, and the outer cover covers the main housing.

42. The essential oil atomizer of claim 41, wherein the outer cover comprises an opening connected to the dispensing opening.

43. The essential oil atomizer of claim 29, wherein the connection opening is arranged at a bottom of the housing.

44. The essential oil atomizer of claim 29, wherein the connection opening comprises a threaded sleeve for connecting the essential oil bottle.

* * * * *